(12) United States Patent
Ruff

(10) Patent No.: US 10,501,494 B2
(45) Date of Patent: Dec. 10, 2019

(54) USES OF PEPTIDES TO TREAT BRAIN INJURY AND DISEASE

(71) Applicant: Michael Ruff, Potomac, MD (US)

(72) Inventor: Michael Ruff, Potomac, MD (US)

(73) Assignee: Creative Bio-Peptides, Potomac, MD (US)

( * ) Notice: Subject to any disclaimer, the term of this patent is extended or adjusted under 35 U.S.C. 154(b) by 0 days.

(21) Appl. No.: 14/263,347

(22) Filed: Apr. 28, 2014

(65) Prior Publication Data

US 2014/0323393 A1 Oct. 30, 2014

Related U.S. Application Data

(60) Provisional application No. 61/816,565, filed on Apr. 26, 2013.

(51) Int. Cl.
*C07K 7/08* (2006.01)
*C07K 7/06* (2006.01)

(52) U.S. Cl.
CPC . *C07K 7/08* (2013.01); *C07K 7/06* (2013.01)

(58) Field of Classification Search
None
See application file for complete search history.

(56) References Cited

U.S. PATENT DOCUMENTS

| | | | |
|---|---|---|---|
| 5,063,206 A | 11/1991 | Bridge et al. | |
| 5,276,016 A | 1/1994 | Pert et al. | |
| 5,514,670 A | 5/1996 | Friedman et al. | |
| 5,534,495 A | 7/1996 | Pert et al. | |
| 5,739,109 A | 4/1998 | Galpin et al. | |
| 5,756,449 A | 5/1998 | Andersen et al. | |
| 5,834,429 A | 11/1998 | Pert et al. | |
| 5,863,718 A | 1/1999 | Pert et al. | |
| 6,011,014 A | 1/2000 | Andersen et al. | |
| 6,242,564 B1 | 6/2001 | Pert et al. | |
| 6,265,374 B1 | 7/2001 | Andersen et al. | |
| 7,390,788 B2 | 6/2008 | Pert et al. | |
| 7,700,115 B2 | 4/2010 | Ruff et al. | |
| 8,916,517 B2 * | 12/2014 | Coy | A61K 33/24 514/1.4 |

OTHER PUBLICATIONS

NIH (<https://www.ninds.nih.gov/Disorders/All-Disorders/Encephalopathy-Information-Page> accessed Aug. 3, 2018).*
Merck Manual (<https://www.merckmanuals.com/professional/neurologic-disorders/peripheral-nervous-system-and-motor-unit-disorders/amyotrophic-lateral-sclerosis-als-and-other-motor-neuron-diseases-mnds> accessed on Aug. 3, 2018).*
Goodwin et al. ("Peptides as therapeutics with enhanced bioactivity" Current Medicinal Chemistry 2012, 19, 4451-4461).*
The Concussion Legacy Foundation (https://concussionfoundation.org/CTE-resources/what-is-CTE, 2019).*
The Mayo Clinic (https://www.mayoclinic.org/diseases-conditions/traumatic-brain-injury/diagnosis-treatment/drc-20378561, 2019).*
Polianova et al., Chemokine receptor-5 (CCR5) is a receptor for the HIV entry inhibitor peptide T (DAPTA), Antiviral Res. 2005. 67:83-92.
Ruff et al., CD4 receptor binding peptides that block HIV infectivity cause human monocyte chemotaxis. Relationship to vasoactive intestinal polypeptide. FEBS Lett. 1987. 211:17-22.
Moore et al. In vivo depression of lymphocyte traffic in sheep by VIP and HIV (AIDS)-related peptides. Immunopharmacology 1988. 16:181-89.
Pert et al. Octapeptides deduced from the neuropeptide receptor-like pattern of antigen T4 in brain potently inhibit human immunodeficiency virus receptor binding and T-cell infectivity. Proc Natl Acad Sci U S A. 1986. 83:9254-9258.
Spisani et al. Chemotactic response of human monocytes to pentapeptide analog derived from immunodeficiency virus protein gp 120. Inflammation. 1990. 14(1):55-60.
Marastoni et al. Synthesis, metabolic stability and chemotactic activity of peptide T and its analogues. J. Peptide Protein Res. 1990. 35:81-88.
Smith et al. Tritiated D-ala-peptide T binding: A pharmacologic basis for the design of drugs which inhibit HIV receptor binding. Drug Development Res. 1988. 15:371-379.
Brenneman et al. Peptide T sequences prevent neuronal cell death produced by the envelope protein (gp120) of the human immunodeficiency virus. Drug Devel Res. 1988. 15:361-369.
Rosi et al. Chennokine receptor 5 antagonist d-ALA-peptide T-amide reduces microglia and astrocyte activation within the hippocampus in a neuroinflammatory rat model of alzheimer's disease. Neuroscience. 2005. 134:671-676.
Owen et al. A theta-defensin composed exclusively of D-amino acids is active against HIV-1. J. Peptide Res.2004. 63:469-76.
Lusso et al., Cryptic Nature of a Conserved, CD4-Inducible V3 Loop Neutralization Epitope in the Native Envelope Glycoprotein Oligomer of CCR5-Restricted, but Not CXCR4-Using, Primary Human Immunodeficiency Virus Type 1 Strains. J Virol. 2005. 79(11):6957-68.

(Continued)

*Primary Examiner* — James H Alstrum-Acevedo
*Assistant Examiner* — Tara L Martinez
(74) *Attorney, Agent, or Firm* — Houtteman Law; Scott Houtteman

(57) ABSTRACT

A method of treating loss of brain function in a patient comprising the steps of preparing a composition comprising a D peptide and a pharmaceutically acceptable carrier. The D peptide has the general structure: A-B-C-D-E-F-G-H in which
   A is Ala, or absent,
   B is Ser, Thr or absent,
   C is Ser, Thr or absent,
   D is Ser, Thr, Asn, Glu, Arg, Ile, Leu,
   E is Ser, Thr, Asp, Asn,
   F is Thr, Ser, Asn, Arg, Gln, Lys, Trp,
   G is Tyr, and
   H is Thr, Ser, Arg, Gly.
All amino acids in the D peptide are the D stereoisomeric configuration. The peptide composition is administered in a therapeutically effective dose.

5 Claims, 3 Drawing Sheets
Specification includes a Sequence Listing.

(56) References Cited

OTHER PUBLICATIONS

Ruff et al., Peptide T[4-8] Is Core HIV Envelope Sequence Required for CD4 Receptor Attachment. Lancet. 1987. 330(8561):751.
Altman et al., Failure of vaccine test is setback in AIDS fight, New York Times, Sep. 22, 2007, 2 pages.
Saez-Torres et al., Peptide T does not ameliorate experimental autoimmune encephalomyelitis (EAE) in Lewis rats, Clin. Exp. Immunol. 2000. 121:151-56.
Yousefzadeh-Chabok et al., "The Relationship Between Serum Levels of Interleukins 6, 8, 10 and Clinical Outcome in Patients with Severe Traumatic Brain Injury." Arch Trauma Res, 2015. 4(1): p. e18357.
Abboud et al., "Inflammation Following Traumatic Brain Injury in Humans: Insights from Data-Driven and Mechanistic Models into Survival and Death." Front Pharmacol, 2016. 7: p. 342.
Padi et aL, "Attenuation of rodent neuropathic pain by an orally active peptide, RAP-103, which potently blocks CCR2- and CCR5-mediated monocyte chemotaxis and inflammation," Pain. Jan. 2012;153(1):95-106.
Song et al., "Effects of an Inhibitor of Monocyte Recruitment on Recovery from Traumatic Brain Injury in Mice Treated with Granulocyte Colony-Stimulating Factor," Int. J. Mol. Sci. Jul. 2, 2017;18(7) 2017.
Morganti et al., "Age exacerbates the CCR2/5-mediated neuroinflammatory response to traumatic brain injury," J. Neuroinflammation. Apr. 18, 2016;13(1):80.

\* cited by examiner

USES OF PEPTIDES TO TREAT BRAIN INJURY AND DISEASE

This application claims the benefit of U.S. Provisional Application Ser. No. 61/816,565, filed Apr. 26, 2013.

The present invention relates, broadly to the treatment or prevention of loss of brain neurons, loss of memory, loss of motor or any other normal function due to concussions, chronic traumatic encephalopathy, mild, moderate, or severe traumatic brain injuries, head trauma, concussive blasts (blastTBI) and neurodegeneration. These conditions can be caused, or associated with, brain inflammation, whether caused by injury, trauma or chronic traumatic encephalopathy. The causes of these conditions include sports injuries, concussive blasts, bacteria, viruses and/or other infective agents, opportunistic infections.

CHRONIC TRAUMATIC ENCEPHALOPATHY, CONCUSSIONS AND BRAIN INJURY

Figure 1:
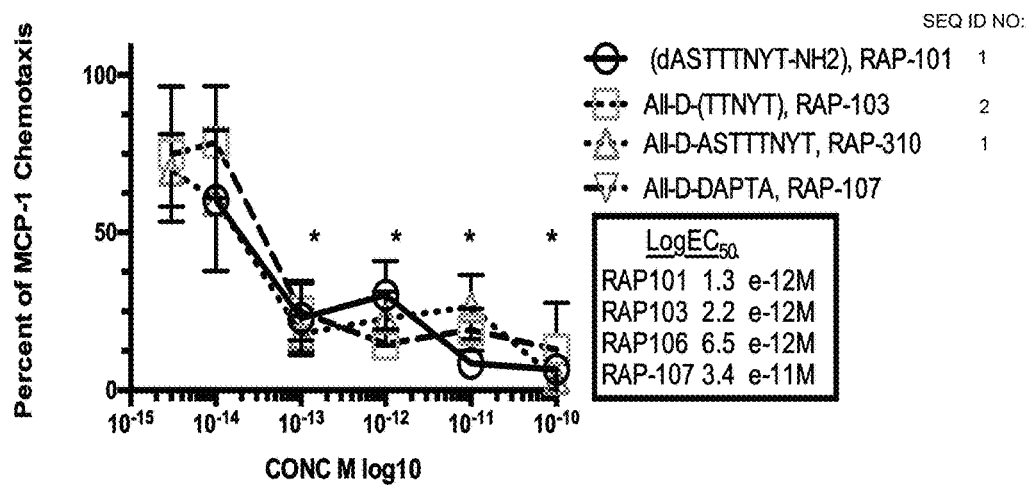
FIG. 1 illustrates the chemotaxis of human monocytes for several all-D analogues of Peptide T.

In particular embodiments, the invention relates to the prevention or treatment of neurodegenerative illnesses which may include chronic traumatic encephalopathy, mild, moderate, or severe traumatic brain injuries, mild traumatic brain injuries, such as from sports or car injuries, injuries from concussions, explosive blasts as occur in war zones (blast TBI), and symptoms or diseases in humans which are associated with chronic immune activation that occurs via cytokine, chemokine, and toll-receptor inflammatory pathways. The invention also relates to pharmaceutical compositions useful in such treatment and/or prevention and to certain active peptides per se. The immune activation may occur as noted and with a abnormal blood-brain-barrier, which would engender more problems with neuroinflammation.

The embodiments teach a general method of how to make small peptides of five to twenty amino acids orally active. The peptides may be used as anti-inflammatory treatments, or as an aid to diagnoses by monitoring the extent of or location in the About 1.7 Million Americans sustain a traumatic brain injury (TBI) each year, ranging from mild to severe, and, in the U.S., this is in addition to about 360,000 soldiers involved in combat operations and public safety workers surviving terrorist attacks who develop mTBI secondary to explosive (concussive) blasts. It contributes about 30% of all injury related deaths and costs about $60B per year. At least 230,000 people are hospitalized due to TBI and survive; more than a million are treated in an ED for TBI and 80,000 to 90,000 Americans experience long-term disability from TBIs.

Clinical issues most frequently seen include: persistent headache; confusion; pain; cognitive/memory problems; frontal lobe or executive function release problems; fatigue; altered sleep patterns; mood changes; and sensory problems including vision or hearing (in some called post-concussion syndrome). TBIs can include both concussions and cerebral contusions, and the term "concussion" can be used interchangeably with the term "mild traumatic brain Injury (mTBI)." However, these cover a spectrum of injury. The mTBI may occur without loss of consciousness. The leading causes of mTBI include motor vehicle accidents (45%); falls (30%); occupational accidents (10%); sports/recreational activities (10%) and assaults (5%). mTBI can be found in 10% of college and 20% of high school players each season.

The neuropathophysiology of mTBI includes primary (immediate) injury (such as direct or indirect contusion resulting in shearing or stretching of brain tissue, cerebral ischemia or stretching of brain tissues), as well as secondary injury, which may begin early and develop and/or last a long time, consisting of, for instance: 1) diffuse axonal injury (DAI), secondary to shear forces in the brain due to sudden deceleration, particularly if the head is rotated; impairments in axonal transport, axonal swelling, Wallerian degeneration and axonal transection. (The axon is part of the neuron that connects it to one or more other neurons—they make up the white matter of the brain.). Cortical contusions due to coup and contrecoup injuries may be seen; and there is a release of excitatory neurotransmitters (Glutamate, acetylcholine, and aspartate) which generates free radicals and excitotoxicity leading to secondary injuries. The blood-brain barrier opens and may remain so for up to a month and possibly longer, with neurotoxic chemicals being leached in (see later). Furthermore, mTBI initiates a progressive neurometabolic cascade that involves ionic shifts, altered brain metabolism, disrupted neuronal connectivity and neurotransmission, as well as significant issues with neuroinflammation.

Using a rat model, another group evaluated the effect of a single 80-psi blast overpressure wave. Histology and immunochemical studies showed an early inflammatory response, tissue damage and the initiation of apoptosis (cell destruction). Regarding neuroinflammation, they found polymorphonuclear leukocytes and lymphocytes infiltrated brain parenchyma within 1 hour post blast. Glial-fibrillary protein, cyclo-oxygenase-2ir, interleukin 1β and tumor necrosis factor were present by 1 hour and remained detectable at 3 weeks post injury.

In another murine trial, evaluating mild "blast type" injuries, a group found long-term impairment of cognition and behavior. Using a moderate to severe brain lateral fluid percussion model, of brain injury in the rat, they found acute increase in interleukin-1α/β and TNF-α levels, macrophage/microglial and astrocytic activation, evidence of increased cellular stress and BBB dysfunction that were present as early as 3-6 hours post injury with both glial activation and BBB dysfunction persisting for at least 18 days post injury.

Neuroinflammation is, as noted above, one of the most important secondary events that begin after the initial cerebral insult. Neuroinflammation has dual and opposing roles, both beneficial and harmful: its effects differ between acute and more delayed phases post injury. Brain injuries take weeks to fully develop after initial insult.

Aside from acute neuroinflammation, mTBI induces long-term and persistent inflammation with elevation of interleukin 1 (IL-1) and other cytokines, as well as increased expression of both beta-amyloid protein and phosphorylated tau protein. This may establish a link between TBI and traumatic dementia. These data highlight the important role of IL-1 in the acute and chronic neuroinflammation post TBI and the possibility of beneficial effects after it is therapeutically inhibited.

Interleukin-1 (IL-1) acts as a proinflammatory cytokine, and is an important mediator of inflammation following a TBI. IL-1 triggers inflammatory reactions, leads to recruitment of leukocytes, disruption of the blood-brain barrier (BBB) and formation of edema. It also induces other interleukins, prostaglandins, histamine, thromboxane, chemokines and adhesion molecules and exerts multiple effects in neuronal, glial and endothelial cells. Elevated levels of IL-1β have been detected intrathecally in patients with head injury, and these elevated levels were found to correlate to poorer clinical outcomes.

The proinflammatory cytokines IL-1α and IL-1β are thought to initiate inflammation and to contribute to neurodegeneration after various brain insults including TBI. Finally, in experimental animal models, intracerebral or intraventricular administration of exogenous IL-1β significantly exacerbates brain injury.

Interleukin-6 (IL-6) promotes inflammatory processes when it stimulates the production of chemokines and adhesion molecules and the recruitment of leukocytes. Studies have demonstrated that increased cerebrospinal fluid (CSF) levels of IL-6 were correlated with the clinical severity of TBI patients.

Tumor necrosis factor-α (TNF-α) is another cytokine with a well-established role in TBI. Elevated levels are observed in the clinical setting of TBI patients. TNF-α has proinflammatory properties similar to IL-1 and it exacerbates inflammation and secondary brain damage post TBI. Early up-regulation of neuronal TNF-α expression after TBI was found to contribute to subsequent neurological dysfunction.

It is now appreciated that the CNS does exhibit features of inflammation mediated for example by astrocytes, and in response to injury, infection or disease, these resident CNS cells generate inflammatory mediators, including proinflammatory cytokines, prostaglandins, free radicals and complement, which in turn induce chemokines and adhesion molecules, recruit immune cells, and activate glial cells. Much of the key evidence demonstrating that inflammation and inflammatory mediators contribute to acute, chronic and psychiatric CNS disorders points to this delicate balance of inflammation and modulation as the tightrope under which so called normalcy functions.

IL-1b, IL-6, and TNF-α are known to be among the major cytokines up-regulated during the acute-phase response to CNS stress and injury. The release of TNF-α and other inflammatory cytokines exacerbates the activation of glial cells and the physiological response switching the Th1 to Th2 cycle and promoting gliosis, inhibiting astrocytic glutamate uptake and inducing apoptosis, particularly in oligodendrocytes thereby contributing to damaging demyelination. The ability to inhibit the action of TNF-α and other inflammatory activators in the early phases of traumatic CNS injury may yield a salutary clinical outcome.

As an illustration, the administration of LPS to animals can prompt severe metabolic and physiological changes which can lead to death and which mimic a condition involving acute inflammation, as in injury, specifically brain injury.

Chronic infusion of LPS into the 4th ventricle of a rat's brain produced an extensive inflammatory reaction throughout the brain, particularly within the hippocampus and temporal lobe regions. Associated with the injection of LPS is the extensive production of TNF-α.

Daily peripheral administration of DAPTA dramatically attenuated the inflammatory response induced by LPS as demonstrated by a decrease in both the number and reactive state of microglial and astrocytes, including significantly reduced levels of NFkB expression within astrocytes in the hippocampus (Rosi, 2005)

Associated with the injection of LPS is the extensive production of tumor necrosis factor alpha (TNF-α). Mice injected with recombinant human TNF-α develop pilo erection of the hair (ruffling), diarrhea and a withdrawn and unkempt appearance, followed by death if sufficient amounts are given. Rats treated with TNF become hypotensive, tachypneic and die of sudden respiratory arrest. Administration of DAPTA (1 mg/Kg) to MethA ascites tumor-bearing mice that were treated with 50 µgm LPS by i.p. injection, had better survival (15/20 in the DAPTA treated group compared to 5/20 in the vehicle control treated group). Thus DAPTA blocks septic shock via innate immune pathways, like the Toll receptors, that cause inflammation in the brain and that are typically activated in injuries.

Diseases

The invention may be useful in the prevention or treatment of human illness or medical conditions, particularly those involving inflammation, such as: chronic traumatic encephalopathy as can occur in sports injuries, concussions, mild, moderate, or severe traumatic brain injuries, immune reconstitution inflammatory syndrome (IRIS) viral, bacterial or drug-induced hepatitis or meningitis; rheumatoid, psoriatic, reactive, or osteo-arthritis or other arthritides, sepsis/septic shock; dermal inflammation, and psoriasis.

More particularly, the invention is useful in treating chronic traumatic encephalopathy, concussions, mild traumatic brain injury, concussive blast injuries, and any brain injuries associated with trauma. In addition to physical trauma, the inflammation caused by viral or bacterial infection can be treated. In addition to direct microbial effects, an immune reconstitution inflammatory syndrome (IRIS) is recognized as a complication of cessation of immunosuppressive therapies for cancer, arthritis, and multiple sclerosis.

Other conditions that would be treated by this class of therapeutic are chronic fatigue syndrome, toxic shock syndrome associated with *Staphylococcus aureus* infection, bowel disease and host-versus-graft response in transplant patients. Such efficacious results in the use of the above compounds is thought to be due, without being limited to any particular theory, to the immunosuppressive activities of these compounds in chronic inflammatory states.

Myelopathy, as already mentioned in being a disorder of the spinal cord, can have many different etiologies most of which are mediated by inflammation include the following:

neurosyphillis;
B12 or folate deficiency;
sarcoidosis;
transverse myelitis;
arachonoiditis;
cervical spondylitis;
motor neuron disease;
neurofibromatosis;
spinal cord compression from tumour, disc or arthritis;
lupus erythematosus of the spinal cord; and
viral encephalomyelitis.

Chronic inflammation or, as more commonly known as chronic immune system activation occurs in response to persistent antigen whose origin may be exogenous or endogenous or may result from an autoimmune state. Such chronic inflammation results in local tissue destruction and depending upon the type of inflammation can result in systemic effects due to the sustained production of inflammatory mediators. Chronic pain, painful neuropathies, diabetic neuropathies are all examples of pain that is caused by immune activation, and stopped or reversed by peptides of this disclosure. Such inflammatory mediators include the cytokines which are soluble mediators produced by activated lymphocytes and macrophages.

Chronic fatigue syndrome (CFS) or chronic fatigue immune dysfunction syndrome is a condition of unknown etiology characterized by a diverse set of signs and systems including severe fatigue, post-exertional malaise, headaches, night sweats, myalgia, ataxia, low grade fever and lymphadenophathy. The serum and cerebrospinal fluid of patients with CFS has been shown to contain increased levels of IL-2, IFN and IL-1 and IL-6.

Rheumatoid arthritis is a disease characterized by autoimmune, chronic inflammation and erosion of joints that may affect up to 3% of the population, including children. Symptoms of rheumatoid arthritis include morning stiffness, swelling and pain upon motion in at least one joint and joint swelling. Extra-articular manifestations of rheumatoid arthritis include vasculitis, cataracts, uveitis, interstitial fibrosis, pericarditis and myocarditis, peripheral neuropathy, myeloid deposits, chronic anemia and subcutaneous and pulmonary nodules.

The present invention deals with the identification of a group of peptides that alleviates the inflammatory response in a number of diseases. These include: brain injury, PML, neuropathies, autoimmune disease, organ transplantation; neoplasia; viral, bacterial, fungal or other infections; and, in particular, any disease wherein infection can manifest in an opportunistic fashion, e.g. during antiviral or immunosuppressive therapy or in any situation where an immunosuppressed state exists, or in immune reconstitution inflammatory syndromes.

Compounds

As will be described below in the experimental data, the mechanism whereby these peptides can alleviate the symptoms of these diseases is dependent on their capability of modulating a whole range of interleukins, chemokines, and their receptors produced by activated cells of the immune system.

More specifically, it has been discovered that a particular group of peptides, particularly those within the group having at least 5 amino acid residues, are very effective agents useful in the treatment of pain after tissue injury and inflammation in general, and are likely to be useful in treating other brain injuries, such as by trauma, neuropathies of all types, and myelopathies, most of which have similar disease mechanisms and occur via inflammation. It remains a significant unmet medical need to develop anti-inflammatory therapies for chronic degenerative illness of humans.

From the above discussion, it is apparent that many symptoms and diseases are associated with chronic inflammation; however, several of these diseases appear to involve different mechanisms. It is therefore important that particular compounds have been found which are useful in treating symptoms and diseases associated with chronic inflammation where it appears that these compounds interact in some manner with receptors of innate immune system cells, such as the chemokine and toll receptors. The compounds relate, as indicated above, to modified derivatives of HIV envelope V2 region peptides such as Peptide T.

All compounds disclosed in the specification are useful for the present invention. The original peptide has its basic point of origin in the octapeptide Ala-Ser-Thr-Thr-Asn-Tyr-Tyr (SEQ ID NO:1). {Pert, 1986}. An analog called Dala1-peptide T-amide ("DAPTA") has been tested as an experimental treatment in humans, with mixed results. Although used in many clinical trials, beneficial results have not been confirmed in controlled trials. The failures of DAPTA in multiple phase 2 clinical studies including HIV {Heseltine}, neuropathies {Simpson}, and multiple sclerosis {Saez-Torres et al., 2000, #49219}, to cite a few published examples, several other non-published examples in psoriasis and multiple sclerosis which are known, indicates that one or more aspects of drug manufacture, dosing, or delivery has not been reduced to practice. In particular, no stable formulation of Dala1-peptide T-amide ("DAPTA") could be shown in earlier examples, indeed the aggregation problems of DAPTA were not even recognized as non-enabling for treatment uses. Proposals for uses in various clinical conditions were speculative.

mDAPTA or RAP-101 is the monomeric form of DAPTA and shows greater potency compared to DAPTA in a manufacturing and formulation dependent manner.

While the primary sequences are identical, mDAPTA differs from DAPTA by existing in a structural conformation with improved stability and biopotency due to procedures that stabilize certain peptide conformations during manufacture. Under strong structure-inducing conditions, as used during manufacture, it is possible to detect medium-range NOEs (Nuclear Overhauser Effects, a probe of spatial proximity) for the first time for this peptide which confirms creation of a novel structure in comparison with earlier NMR and computational studies {Yang et al., 2009, #89392}.

Further, none of the subject disease uses has curative treatments indicating substantial progress remains to deliver effective medicines and that continued drug development encompassing both formulation, dosing, and targets of action is required for enablement of the Peptide T series of peptides.

That peptide has been identified from the V2 subregion of the human immune deficiency virus (HIV) external glycoprotein molecule gp120, which is responsible for binding to any cell carrying any one of several chemokine or neuropeptide receptors related to GHRH, VIP, and PACAP. The receptors for the peptides here described are present in nervous and immune cells, and, in particular, helper lymphocytes, microglial cells in the CNS, monocytes and dendritic cells.

By targeting the cells of innate immunity the peptides can be used in pharmaceutical compositions and compositions of matter for treating and preventing any disease or condition caused by an organism, compound or immune dysfunction that results in an inflammatory reaction of the immune system. In particular, those inflammatory reactions that occur in, or adjacent to nervous tissue, such as the brain or spinal cord.

The peptides or peptide formulations may be used alone or in combination with any other pharmaceutically active compound, such as an anti-infective agent, for example an antibiotic and/or antiviral agent and/or antifungal agent, or another pharmaceutically active compound, such as a neuroprotective agent, or more specifically to block excitatory amino acid neurotoxicity.

The peptides may be administered orally, bucally, parenterally, topically, rectally, vaginally, by intranasal inhalation spray, by intrapulmonary inhalation or in other ways. In particular, the peptides according to the invention may be formulated for topical use, for inhalation with spray or powder, for injection (for example subcutaneous, intramuscular, intravenous, intra-articular or intra-cisternal injection), for infusion or for oral administration and may be presented in unit dose form in ampoules or tablets or in multidose vials or other containers with an added perservative. The compositions may take such forms as suspensions, solutions, or emulsions or gels in oily or aqueous vehicles, and may contain formulatory agents such as suspending, stabilising and/or dispersing agents. Alternatively, the active ingredient may be in powder and/or lyophilised form for direct administration or for constitution with a suitable vehicle (e.g. sterile, pyrogen-free water, normal saline or mannose, dextrose, other sugars or sugar-like additives) before use. The pharmaceutical compositions containing peptides(s) may also contain other active ingredients such as antimicrobial agents, or preservatives.

The compositions may contain from 0.001-99% (w/v or, preferably, w/w) of the active material.

The compositions are administered in therapeutically or prophylactic effective does, i.e. 0.05-500 mg of peptide per day. Very large doses may be used as the peptide according to the invention is non-toxic. However, normally this is not required. The dose administered daily of course depends on the degree of inflammation and inflammatory response.

For administration by injection or infusion of the compositions, the daily dosage, as employed for treatment of adults of approximately 70 kg of body weight, will often range from 0.2 mg to 25 mg of active material which may be administered in the form of 1 to 4 doses over each day.

An unexpected and non-obvious aspect of the present invention is the use of all-D amino-acids in the creation of the bioactive peptides.

Figure 3:
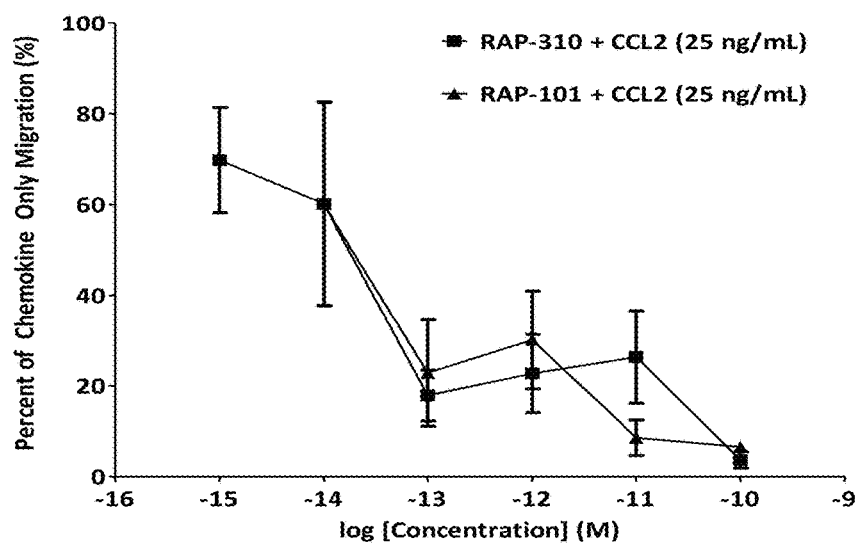
FIG. 3 illustrates a side by side comparison of an all D pentapeptide with its mostly L pentapeptide isomer.
Figure 4:
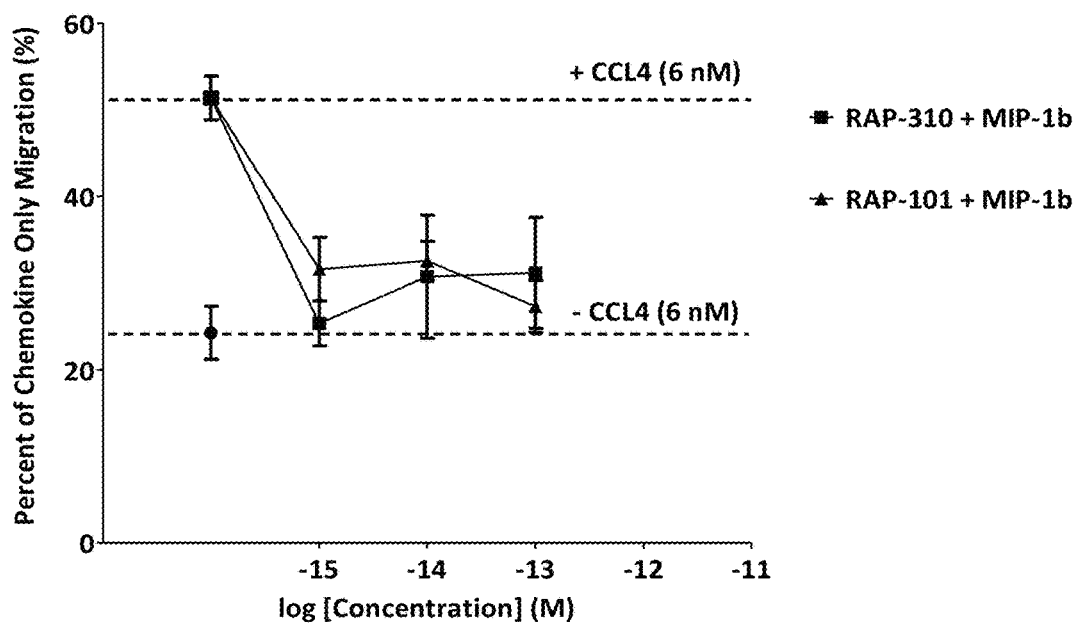
FIG. 4 illustrates a peptide's potency at low (sub-pM) concentrations in blocking CCR5-mediated human monocyte chemotaxis.

The result is surprising in view of an earlier study, Pert {Pert, 1986}, FIGS. 3 and 4, which showed that that D for L substitutions in linear peptide of General Formula 1, of which the specific example is ASTTTNYT (SEQ ID NO:1) can cause great loss of potency.

Having one D substitution, in the specific position No1, (the D-ala) retains potency.

Making an additional D substitution, in the specific position No 8 (the D-Thr) results in loss of 99 to 99.9% of the activity. Thus it is shown that introduction of L to D substitutions can not be made in a general fashion, and that these modifications can, and typically do, destroy biopotency by disrupting the peptide structure required for receptor potency.

This point is further made in Brenneman, 1988 {Brenneman, 1988, drug}, with specific reference to the peptide TTNYT (SEQ ID NO:2). See FIG. 2 and Table 1. Upon making the L to D substitution in position 4 (Tyr), the peptide completely loses activity.

A detailed study of the peptide TTNYT (SEQ ID NO:2) and L to D substations was published in Smith, 1988 {Smith et al., 1988, #34265}, Refer to FIG. 3. Introduction of single L to D substitutions in each position 1, 2, 3, 4, results in loss of potency, and all of the D form substitutions are substantially less active (50×) to completely inactive.

As such the use of D-substitutions by Andersen in "each" position has not been reduced to practice. The data shows that in no instance does a D for L amino-acid substitution achieve comparable potency to the all-L form, rather D substitutions result in loss of activity, sometimes complete loss of biopotency in a position dependent fashion.

The notion that an all-D peptide would retain significant potency is furthermore novel in consideration of long accepted art of Stewart and Woolley {Stewart and Woolley, 1965, #22293} who prepared all-D peptides. For example, from their article, "In contrast to the change of a single residue, the inversion of all the amino-acid residues in a pentapeptide which has hormonal activity of MSH was found to cause loss of hormonal activity . . . "

Further in this paper the authors write "because there is as yet no general method for predicting the structural requirements required to make antimetabolites of peptides, we synthesized all-D bradykinin (note 9 amino acids, similar size to the 8 amino acid Formula 1 peptide of Andersen) in an effort to find out whether inversion of all the amino-acids of a peptide may be a generally applicable method for synthesis of peptide antagonsits."

The authors then concluded: "Amounts of all-D-bradykinin up to 50,000 times the the standard challenge of bradykinin showed neither any inhibition of the response to bradykinin, or any bradykinin-like effect. It would thus seem that inversion of all the amino-acid residues may not be a generally applicable method for formation of antimetabolites of biologically active peptides".

In contrast to the repeated findings of numerous authors (op. cit. above) the current study discovered, while seeking to construct a negative control, inactive version of linear octapeptide of General Formula 1 (defined below), that a linear octapeptide of General Formula 1 comprised of all-D-amino-acid substitutions, as well as all-D-amino-acid substitutions of linear pentapeptide analogs of the linear octapeptide of General Formula 1, do retain comparable potency as the all-L or single-D-substituted peptides first described in Pert {Pert, 1986}. Thus there was no appreciable loss of potency, a result unexpected in view of Smith {Smith et al., 1988, #34265}, and Brenneman {Brenneman et al., 1988, #9180} with specific reference to the peptide TTNYT (SEQ ID NO:2).

The ability to make D for L amino acid substitutions however creates the possibility to make peptides orally deliverable drug compounds. Stability of peptides in biological fluids, such as plasma, or digestive enzymes has limited their utility as drugs. The ability to create all-D peptides that retain potency is an unexpected general method of creating peptides of General Formula 1, and likely many others, which may be stabilized to proteolysis, while retaining biopotency, so a therapeutic may be administered to people via oral dosing or otherwise enjoy enhanced bioavailability in the body.

According to a first aspect of the present invention, there is provided the use of a linear peptide of General Formula 1 wherein all amino acids are in the D-stereoisomeric configuration:

A-B-C-D-E-F-G-H.                    General Formula 1 wherein:

A is Ala, or absent,
B is Ser, Thr or absent,
C is Ser, Thr or absent,
D is Ser, Thr, Asn, Glu, Arg, Ile, Leu,
E is Ser, Thr, Asp, Asn,
F is Thr, Ser, Asn, Arg, Gln, Lys, Trp,
G is Tyr, and
H is Thr, Ser, Arg, Gly.

All of the amino acids referred to in General Formula 1 will be in the D-stereoisomeric configuration and candidates for H may be esterified, glycosylated, or amidated. The peptide comprises at least 5 amino acids. The all-L amino acid version of a linear peptide of General Formula 1 has been called Peptide T {Pert, 1986}.

Peptides useful in the invention may be administered as a composition in conjunction with a pharmaceutically acceptable carrier.

In this way the peptides can be used in pharmaceutical compositions and compositions of matter for treating and preventing any disease or condition caused by an organism, compound or immune dysfunction that results in an inflammatory reaction of the immune system. The peptides or peptide formulations may be used alone or in combination with any other pharmaceutically active compound, such as an anti-infective agent, for example an antibiotic and/or antiviral agent and/or antifungal agent, or another pharmaceutically active compound, such as an antineoplastic agent.

The invention will now be illustrated by the following non-limiting examples. The examples refer to the accompanying drawings, in which:

All-D peptide analogs of Peptide T (ASTTTNYT (SEQ ID NO:1), Pert, 1985) inhibit CCL2-mediated human monocyte chemotaxis.

An example is provided in FIG. 1. We synthesized three all-D-amino acid peptide analogs of DAPTA, such as all-D-ASTTTNYT (SEQ ID NO:1)-NH2 (RAP-107), all-D-Peptide ASTTTNYT (SEQ ID NO:1) (RAP-310), and the shorter pentapeptide All-D-TTNYT (SEQ ID NO:2) (RAP-103) that contains the core bioactive moiety of Peptide T {Ruff, Hallberg, 1987}.

The results show that all three "all-D" peptides, comprised of all D, no L, amino acids retained nearly full potency. As expected DAPTA, with 7 of 8 amino-acids as L form, was most potent and the other all-D amino-acid peptides were some 2 to 35-fold reduced in potency. The potency reductions will not affect clinical usefulness as all of the compounds are active at sub-nM and pM concentrations to antagonize chemokine receptors.

Legend: The effect of all-D amino acid derivatives ("RAPs", generic names) of Peptide T (all-L-ASTTTNYT (SEQ ID NO:1))(Pert, 1986), the V2 derived antagonist of CCR5/CCR2 mediated HIV infection and inflammation, to block CCL2 (MCP-1) chemotaxis was studied. Triplicate determinations were made and results are expressed as the mean plus or minus SEM. The experiment shown is a direct comparison among all RAPs. Statistical analysis was by unpaired t-test, with significance set at the p<0.01 (*) level for difference from CCL2 only chemotaxis.

Converting peptides of general formula 1 (ASTTTNYT (SEQ ID NO:1)) to all-D-amino acids retain similar receptor targets, and similar receptor potencies to block innate immune responses. FIG. 1 illustrates the activity of all-D compared to mostly L-form peptides of formula I. It is shown that three related peptides of general formula I, that have identical primary sequence or that share partial sequence, differing only in enantiomeric form, block CCL2 chemotaxis. The results are unexpected in view of {Pert, 1986; Brenneman et al., 1988, #9180; Ruff; Smith et al., 1988, #34265; Stewart and Woolley, 1965, #22293} which show that most L to D substitutions show reduced activity, and some cause complete loss of biopotency. The tyrosine moiety is particularly sensitive and the peptides are not active in L-form with a D-tyrosine.

We broadened (FIG. 2) the list of efficacious all-D-peptides to include eight more unique examples (Ser-Ser-Thr-Tyr-Arg SEQ ID NO:3, Thr-Thr-Ser-Tyr-Thr SEQ ID NO:4, Asn-Thr-Arg-Tyr-Arg SEQ ID NO:5, Ile-Asp-Asn-Tyr Thr SEQ ID NO:6, Asn-Thr-Ser-Tyr-Arg SEQ ID NO:7, Ile-Asn-Asn-Tyr-Thr SEQ ID NO:8, Asn-Thr-Ser-Tyr-Gly SEQ ID NO:9, Glu-Thr-Trp-Tyr-Ser SEQ ID NO:10) of HIV envelope gp160 and more commonly gp120-V2 region, near the bridging sheet, at approximately amino-acid 185 in the V2-loop of the envelope protein, depending on HIV env isolate. The synthetic derived all-D-pentapeptides with a tyrosine in the fourth position, and Ser, Thr, or Asp in the second position, that potently block CCR2/CCR5 chemotaxis are broad spectrum chemokine receptor antagonists useful as potential orally active peptide therapeutics. The difficulty of development of orally active peptides has greatly impeded their development as therapies. Here we suggest a general method to stabilize peptides to proteolytic degradation that preserves biopotency, either as an agonist or as an antagonist of cell surface receptors.

Figure 2:
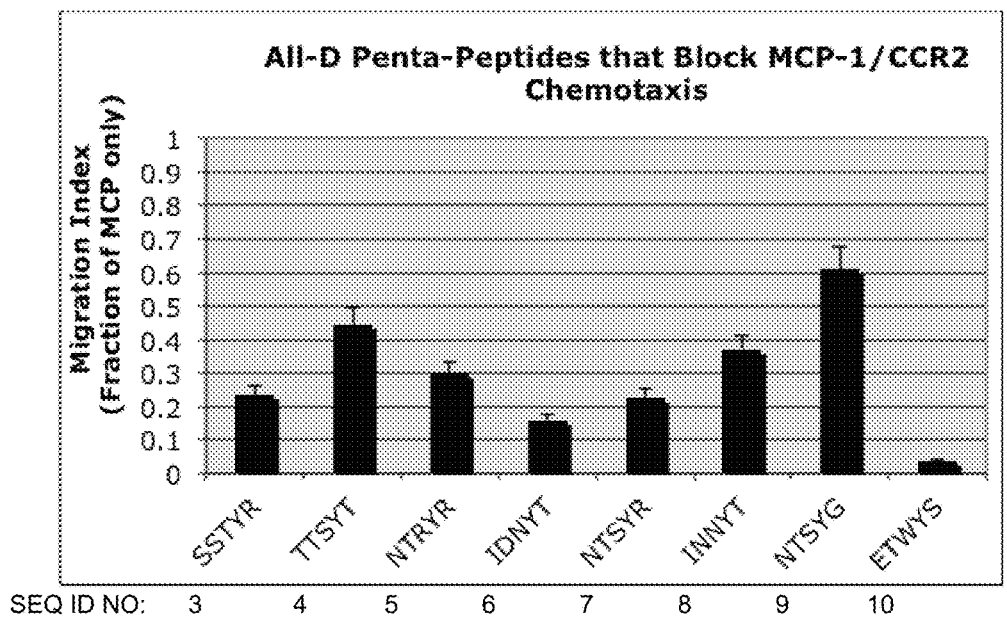
FIG. 2 illustrates chemotaxis of human monocytes for several all D pentapeptides.

Turning to FIG. 2, an All-D-pentapeptides inhibits CCR2 (MCP-1) elicited chemotaxis of human monocytes. Purified human monocytes were treated with 20 pM of All-D-pentapeptides for 30 minutes prior to chemotaxis against human MCP-1 (0.6 nM) for 2 hours. The chemotactic index (ratio of migration for CCR2/buffer) for MCP-1 was 3-4. A representative experiment is shown comprising triplicate determinations and is presented as relative fluorescence units, Mean±SEM. The activity of All-D-pentapeptide TTNYT (SEQ ID NO:2) (RAP-103) to block MCP-1 human monocyte chemotaxis has been published, {Padi, 2012}.

The peptides share activity to block diverse chemokine receptors. Thus we show that DAPTA, the prototype octapeptide (D-Ala$_1$-STTTNYT-NH2) blocks chemokine receptor 8 (CCR8) and the all-D-ASTTTNYT (SEQ ID NO:1) analog also blocks CCR8, with comparable potency. Thus again, with a different receptor target, the all-D peptide performs very similarly to its mostly L-amino acid prototype first described in Pert, 1986. (FIG. 3).

Effectiveness of Dala1-ASTTTNYT (SEQ ID NO:1)-NH2 and all-D-TTNYT (SEQ ID NO:2) to have anti-inflammatory effects by lowering neurotoxic cytokines in people or animals. We show (Table 1) that the all-D-TTNYT (SEQ ID NO:2) pentapeptide analog (RAP-103) of Dala1-ASTTTNYT (SEQ ID NO:1)-NH2 (DAPTA/RAP-101) has comparable in vivo actions to normalize elevated inflammatory cytokines Thus the all-D amino acid substitutions are well tolerated and retain biopotency.

TABLE 1

SUMMARY OF INFLAMMATORY BIOMARKER CHANGES FOR DAPTA/RAP-101 AND ALL-D-TTNYT (SEQ ID NO: 2) (RAP-103) RELEVANT TO AD.

| Biomarker | Species | Change | DRUG | Reference |
|---|---|---|---|---|
| IL-1 | Hu | decrease | RAP-101 | Ruff, 2003 |
| IL-6 | Hu | decrease | RAP-101 | Ruff, 2003 |
| IL-8 | Hu | decrease | RAP-101 | Ruff, 2003 |
| TNF-α | Hu | decrease | RAP-101 | Ruff, 2003 |
| MCP-1 | Rat | decrease | RAP-103 | unpublished |
| MIP-1α | Rat | decrease | RAP-103 | unpublished |
| TNF-α | Rat | decrease | RAP-103 | unpublished |
| CCL2 | Rat | decrease | RAP-103 | unpublished |
| CCL3 | Rat | decrease | RAP-103 | unpublished |
| CCR2 | Rat | decrease | RAP-103 | unpublished |
| CCR5 | Rat | decrease | RAP-103 | unpublished |
| IL-1β | Rat | decrease | RAP-103 | Padi, 2012 |
| IL-6 | Rat | decrease | RAP-103 | Padi, 2012 |

Functional Antagonism of CCL2/CCR2-Mediated Chemotaxis by Mostly L-Amino Acid Peptide DAPTA (RAP-101) and the All-D-[ASTTTNYT] (RAP-310) Analog.

In this example the parent peptide is DAPTA (RAP-101), which has only the one D-amino acid in position 1. It is compared for biopotency with an all-D amino acid close analog whereby all of the amino acids are made in the D form (RAP-310) to block the CCR2 chemokine receptors.

In FIG. 3, RAP-101 (which refers to monomeric DAPTA, U.S. Pat. No. 7,390,788) and RAP-310 potently block CCL2(MCP-1) elicited chemotaxis of human monocytes. Elutriated human monocytes were treated with indicated doses of RAP-101 and RAP-310 for 30 minutes prior to chemotaxis against human CCL2 (25 ng/mL) for 2 hours. Data shown is the average of triplicate determinations from two separate experiments presented as Mean±SEM The log EC50 for inhibition of CCL2 by RAP-101 and RAP-310, generated by a nonlinear inhibition curve fit analysis on GraphPad Prism 6.0 software:

$$IC50 \text{ for RAP-310+CCL2(25 ng/mL)} IC50=6.5\times10^{-12} M$$

$$IC50 \text{ for RAP-101+CCL2(25 ng/mL)} IC50=1.3\times10^{-12} M$$

Conclusion: RAP-310 and 101 are potent to block CCL2 mediated chemotaxis. RAP-310, an analog of RAP-101 which was modified for oral bioavailability, shows minimal loss of potency in blocking CCL2-elicited chemotaxis of human monocytes compared to RAP-101, its intranasally active octapeptide analog.

Functional Antagonism of MIP-1β (CCL4)/CCR5: Chemotaxis by D-Ala1-STTTNYT-NH2/RAP-101 and All-D-[ASTTTNYT] (RAP-310)

In this example the parent peptide is DAPTA (RAP-101), which has only the one D-amino acid in position 1. It is compared for biopotency with an all-D amino acid close analog whereby all of the amino acids are made in the D form (RAP-310) to block the CCR5 chemokine receptors. Here we compare RAP-101 and RAP-310 for antagonism of CCR5 in purified human monocytes by blocking the CCR5 ligand MIP-1β/CCL4 in chemotaxis. The peptides show comparable potency to block CCR5-mediated human monocyte chemotaxis at low (sub-pM) concentrations.

In FIG. 4, D-Ala1-STTTNYT-NH2/RAP-101 and All-D-[ASTTTNYT (SEQ ID NO:1)] (RAP-310) inhibit MIP-1β elicited chemotaxis of human monocytes treated with GM-CSF for 48 hours. Human monocytes were treated with indicated doses of RAP-310 and RAP-101 for 10 minutes prior to chemotaxis against MIP-1β (50 ng/mL) for 2 hours. Data are the average of triplicate determinations. Data are presented as Mean±SEM.

RAP-103 (all-D-TTNYT (SEQ ID NO:2)) Blocks the innate immune Toll4 (TLR4) receptor which mediates the inflammatory effects of LPS and bacterial products in septic shock.

Figure 5:
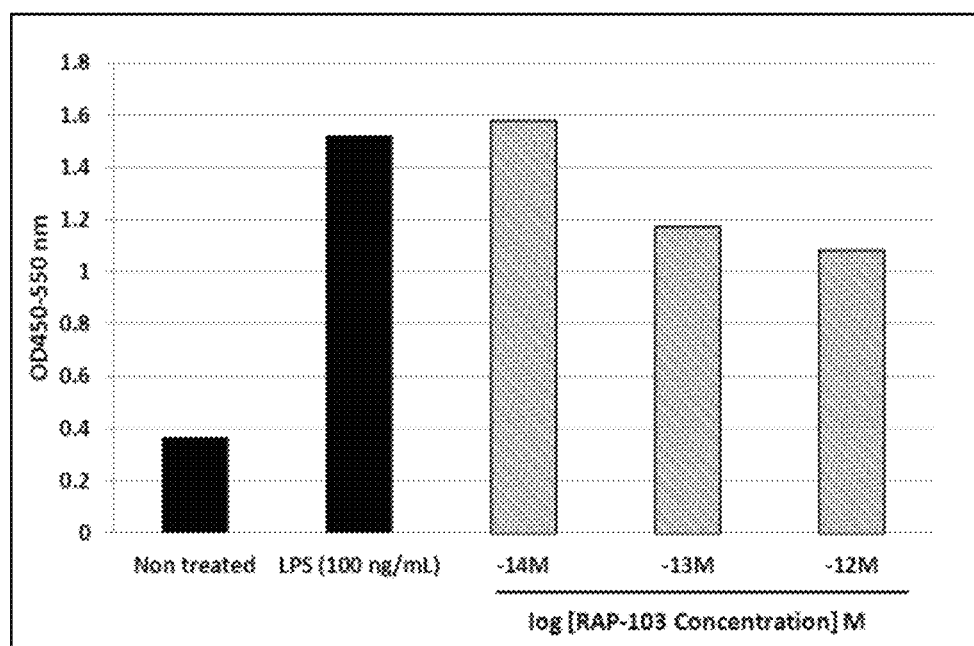
FIG. 5 illustrates RAP 103 inhibition of lipopolysaccharide (LPS) induction of TNF-α secretion in monocyte-derived iDC.

The ability to make potent antagonists of innate immunity chemokine receptors and TLR4 receptors by employing all-D-substitutions for pentapeptides of the General Formula 1 wherein all amino acids are in the D-stereoisomeric configuration is shown in the next example (FIG. 5).

We studied blocking of TLR4 effects of the mostly L-amino acid octapeptide DAPTA/RAP-101 compared to a shorter and all-D amino acid analog TTNYT (SEQ ID NO:2)/RAP-103, which blocks inflammation, cytokine secretion and monocyte infiltration in a nerve injury model {Padi}. RAP-101, previously shown to block LPS/TLR4 induced brain microglial activation {Rosi} in animal models. We wanted to evaluate the bioactivity of the shorter, all-D analog, RAP103. Here we show RAP-103 inhibition of TLR4 induced TNF-α secretion, an important neurotoxic pathway in brain injury and inflammation. Thus both a majority L-amino acid peptide, and a shorter all-D analog, RAP-103, are both shown to block TLR4.

In FIG. 5 LPS induces TNF-α secretion in monocyte-derived iDC. Cells were incubated for 5 h in medium alone or LPS only at a concentration of 100 ng/mL (black columns), or medium containing LPS plus RAP103 (All-D-TTNYT (SEQ ID NO:2)) (light grey columns). Supernatants were analyzed for secreted TNF-α after 5 hours. The bars represent absorbance in an ELISA assay and correspond to TNF-α levels.

The $IC_{50}$ for RAP103 inhibition of TNF-α production was approximately $10^{-13}$ M. The effect of RAP103 to block TLR4 may be allosteric or act via an accessory protein, and may be upstream of chemokine receptor activation since TLR4 signaling typically releases chemokines and cytokines

LITERATURE CITED

Brenneman, D. E., J. M. Buzy, M. R. Ruff, and C. B. Pert. 1988. Peptide T sequences prevent neuronal cell death produced by the envelope protein (gp120) of the human immunodeficiency virus. Drug Devel Res. 15:361-369

Heseltine, P. N., K. Goodkin, J. H. Atkinson, B. Vitiello, J. Rochon, R. K. Heaton, E. M. Eaton, F. L. Wilkie, E. Sobel, S. J. Brown, D. Feaster, L. Schneider, W. L. Goldschmidts, and E. S. Stover. 1998. Randomized double-blind placebo-controlled trial of peptide T for HIV-associated cognitive impairment. Arch Neurol. 55:41-51

Padi, S. S., X. Q. Shi, Y. Q. Zhao, M. R. Ruff, N. Baichoo, C. B. Pert, and J. Zhang. 2012. Attenuation of rodent neuropathic pain by an orally active peptide, RAP-103, which potently blocks CCR2- and CCR5-mediated monocyte chemotaxis and inflammation. Pain. 153:95-106.

Pert, C. B., J. M. Hill, M. R. Ruff, R. M. Berman, W. G. Robey, L. O. Arthur, F. W. Ruscetti, and W. L. Farrar. 1986. Octapeptides deduced from the neuropeptide receptor-like pattern of antigen T4 in brain potently inhibit human immunodeficiency virus receptor binding and T-cell infectivity. Proc Natl Acad Sci USA. 83:9254-928.

Rosi, S., C. B. Pert, M. R. Ruff, K. Gann-Gramling, and G. L. Wenk. 2005. Chemokine receptor 5 antagonist D-Ala-peptide T-amide reduces microglia and astrocyte activation within the hippocampus in a neuroinflammatory rat model of Alzheimer's disease. Neuroscience. 134:671-676

Ruff, M. R., P. L. Hallberg, J. M. Hill, and C. B. Pert. 1987a. Peptide T[4-8] is core HIV envelope sequence required for CD4 receptor attachment [letter]. Lancet. 2:751

Ruff, M. R., B. M. Martin, E. I. Ginns, W. L. Farrar, and C. B. Pert. 1987b. CD4 receptor binding peptides that block HIV infectivity cause human monocyte chemotaxis. Relationship to vasoactive intestinal polypeptide. FEBS Lett. 211:17-22

Saez-Torres, I., C. Espejo, J. J. Perez, N. Acarin, X. Montalban, and E. M. Martinez-Caceres. 2000. Peptide T does not ameliorate experimental autoimmune encephalomyelitis (EAE) in Lewis rats. Clin Exp Immunol. 121:151-156

Simpson, D. M., D. Dorfman, R. K. Olney, G. McKinley, J. Dobkin, Y. So, J. Berger, M. B. Ferdon, and B. Friedman. 1996. Peptide T in the treatment of painful distal neuropathy associated with AIDS: results of a placebo-controlled trial. The Peptide T Neuropathy Study Group. Neurology. 47:1254-1259

Smith, C. C., P. L. Hallberg, P. Sacerdote, P. Williams, E. Sternberg, B. Martin, C. Pert, and M. R. Ruff. 1988. Tritiated Dala1-peptide T binding: A pharmacologic basis for the design of drugs which inhibit HIV receptor binding. Drug Devel Res. 15:371-379

Stewart, J. M., and D. W. Woolley. 1965. All-D-bradykinin and the problem of peptide antimetabolites. Nature. 206: 619-620

Yang, T. C., J. Rendell, W. Gulliver, and V. Booth. 2009. Peptide T exhibits a well-defined structure in fluorinated solvent at low temperature. J Pept Sci. 15:818-823.

What is claimed is:

1. A method of treating brain trauma in a patient comprising the steps of: preparing a composition comprising a D peptide and a pharmaceutically acceptable carrier, said D peptide further comprises at most twenty (20) D amino acid residues in length and contains five contiguous D amino acid residues having the sequence Thr-Thr-Asn-Tyr-Thr (SEQ ID NO: 2), and administering said composition to the patient in a therapeutically effective dose, wherein said composition acts to treat the brain trauma in the patient, and wherein said brain trauma is traumatic brain injury.

2. The method as defined in claim 1 wherein said administering of said composition to the patient is selected from the group consisting of administering: orally, bucally, parenterally, topically, rectally, vaginally, by intranasal inhalation spray or by intrapulmonary inhalation.

3. The method as defined in claim 1 further comprising, said D peptide is at most twelve (12) D amino acid residues in length.

4. The method as defined in claim 1 further comprising, said D peptide is at most eight (8) D amino acid residues in length.

5. The method as defined in claim 1 further comprising, said D peptide is five (5) D amino acid residues in length.

* * * * *

SEQUENCE LISTING

<160> NUMBER OF SEQ ID NOS: 10

<210> SEQ ID NO 1
<211> LENGTH: 8
<212> TYPE: PRT
<213> ORGANISM: Human immunodeficiency virus

<400> SEQUENCE: 1

Ala Ser Thr Thr Thr Asn Tyr Thr
1               5

<210> SEQ ID NO 2
<211> LENGTH: 5
<212> TYPE: PRT
<213> ORGANISM: Human immunodeficiency virus

<400> SEQUENCE: 2

Thr Thr Asn Tyr Thr
1               5

<210> SEQ ID NO 3
<211> LENGTH: 5
<212> TYPE: PRT
<213> ORGANISM: Human immunodeficiency virus

<400> SEQUENCE: 3

Ser Ser Thr Tyr Arg
1               5

<210> SEQ ID NO 4
<211> LENGTH: 5
<212> TYPE: PRT
<213> ORGANISM: Human immunodeficiency virus

<400> SEQUENCE: 4

Thr Thr Ser Tyr Thr
1               5

<210> SEQ ID NO 5
<211> LENGTH: 5
<212> TYPE: PRT
<213> ORGANISM: Human immunodeficiency virus

<400> SEQUENCE: 5

Asn Thr Arg Tyr Arg
1               5

<210> SEQ ID NO 6
<211> LENGTH: 5
<212> TYPE: PRT
<213> ORGANISM: Human immunodeficiency virus

<400> SEQUENCE: 6

Ile Asp Asn Tyr Thr
1               5

```
<210> SEQ ID NO 7
<211> LENGTH: 5
<212> TYPE: PRT
<213> ORGANISM: Human immunodeficiency virus

<400> SEQUENCE: 7

Asn Thr Ser Tyr Arg
1               5

<210> SEQ ID NO 8
<211> LENGTH: 5
<212> TYPE: PRT
<213> ORGANISM: Human immunodeficiency virus

<400> SEQUENCE: 8

Ile Asn Asn Tyr Thr
1               5

<210> SEQ ID NO 9
<211> LENGTH: 5
<212> TYPE: PRT
<213> ORGANISM: Human immunodeficiency virus

<400> SEQUENCE: 9

Asn Thr Ser Tyr Gly
1               5

<210> SEQ ID NO 10
<211> LENGTH: 5
<212> TYPE: PRT
<213> ORGANISM: Human immunodeficiency virus

<400> SEQUENCE: 10

Glu Thr Trp Tyr Ser
1               5
```